United States Patent
Belew et al.

(10) Patent No.: US 7,006,211 B1
(45) Date of Patent: Feb. 28, 2006

(54) AERIAL UTILITY INSPECTION METHOD AND APPARATUS

(75) Inventors: Michael Shane Belew, Columbus, OH (US); Hossein Eslambolchi, Los Altos Hills, CA (US); John Sinclair Huffman, Conyers, GA (US)

(73) Assignee: AT&T Corp., New York, NY (US)

( * ) Notice: Subject to any disclaimer, the term of this patent is extended or adjusted under 35 U.S.C. 154(b) by 424 days.

(21) Appl. No.: 10/292,132

(22) Filed: Nov. 12, 2002

(51) Int. Cl.
*G01N 21/00* (2006.01)

(52) U.S. Cl. .................. 356/237.1; 174/93; 174/60; 250/234

(58) Field of Classification Search .. 356/237.1–237.5, 356/73.1; 182/14; 174/5 R, 60, 93; 250/234; 474/273; 324/222; 254/134.5, 134.3 R
See application file for complete search history.

(56) References Cited

U.S. PATENT DOCUMENTS

| | | | |
|---|---|---|---|
| 3,641,348 A | * | 2/1972 | Schwarz ..................... 250/334 |
| 4,908,482 A | * | 3/1990 | Shimirak et al. ............. 174/93 |

FOREIGN PATENT DOCUMENTS

| | | | |
|---|---|---|---|
| JP | 59222755 | * | 12/1984 |
| JP | 363103953 A | * | 5/1988 |
| JP | 401103110 A | * | 4/1989 |
| JP | 402074111 A | * | 3/1990 |
| JP | 404013963 A | * | 1/1992 |
| JP | 405038012 A | * | 2/1993 |
| JP | 406133422 A | * | 5/1994 |

* cited by examiner

*Primary Examiner*—Hoa Q. Pham

(57) ABSTRACT

An Aerial Inspection system is presented. The Aerial Inspection system includes an Aerial Inspection device. The Aerial Inspection device includes an upper section and a lower section. A passageway is formed within the Aerial Inspection device when the upper section and the lower section are connected. The passageway runs the length of the Aerial Inspection device. The passageway envelops a cable. Wheels connected to the upper section of the Aerial Inspection device protrude into the passageway and make contact with the cable. The Aerial Inspection device (e.g., the wheels) rests on the cable during operations. Cameras are positioned in the Aerial Inspection device to view the cable. As the wheels rotate, the Aerial Inspection device moves along the cable taking images of the cable. The cameras transmit images to a display for viewing or store the images for processing. As a result, faults in the cable may be detected and viewed from the ground or a remote location.

16 Claims, 2 Drawing Sheets

AERIAL UTILITY INSPECTION METHOD AND APPARATUS

BACKGROUND OF THE INVENTION

1. Field of the Invention

This invention relates to troubleshooting. Specifically, the present invention relates to cable troubleshooting.

2. Description of the Related Art

Utility companies provide service to customers. Whether the Utili8ty Company is a power company or a communications company, the Utility Company uses a utility conveyance to provide the service to customers. A utility conveyance typically includes the cables and mechanisms for transporting the Utility Company service to customers.

Cabling is a widely deployed mechanism (e.g., utility conveyance) for transporting Utility Company services. For example, copper cabling, coaxial cabling and fiber-optic cabling are all common types of cabling used to deploy services. The cabling typically spans the distance from the source to the destination (e.g., customer).

The cabling is often placed in locations that are unobtrusive so that the likelihood of damage to the cable is minimized and as a result, service is not disrupted. Therefore, cables are often placed in subterranean locations as well as locations above the earth for protection from damage. For example, cables are often run in trenches or cables are strung many feet (e.g., 15–50) above the earth between support poles.

However, whether the cables are placed in a subterranean environment or strung between support poles, the cables are still subject to activities that may damage the cables. For example, when cables are strung between support poles, lightening may strike the cables, high winds may damage the cables, or a hailstorm may cause damage. When these cables are damaged, they need to be fixed to avoid or minimize a disruption in service.

Service technicians are typically dispatched to isolate and repair the cable damage. Whether the cables are in a subterranean environment or strung between support poles, the technicians first isolate the fault in the damaged cable and then proceed with the cable repair. For example, if communication cable carrying optical fibers are strung between poles, a technician would first need to isolate the fault in the outer sheath of the cable and then proceed to repair the optical fibers.

However, a number of problems arise when a technician attempts to isolate a fault in a cable that is strung between support poles. For example, since the cable is about 25 to 30 feet above the earth it is difficult to see the faults in these cables from the ground. In addition, even if the technician were to climb the support pole to view the damaged cable, since the poles are positioned a certain distance apart, it may be difficult to see the fault after climbing the poles.

A number of conventional techniques have been developed to isolate and more accurately define the location of damage or faults in cables strung between support poles. For example, when fiber optic cable is strung between support poles, an Optical Time-Domain Reflectometer (OTDR) may be used to more accurately locate the fault in the cable. The OTDR may isolate the fault to a location between two support poles.

However, even with a technique that isolates the location of a fault, problems arise. First, the OTDR may not have a fine calibration and as such the fault may be isolated to a span of cable that is tens of feet long. Second, in order to troubleshoot the fault the technician must see the fault. However, it is difficult to see the fault from the ground. Even using binoculars it is difficult to steady the human hand enough to isolate and see the fault. In addition, depending on where the fault is located between two support poles, it may be difficult to see the fault from either pole. Lastly, taking the cable down or bringing in machinery to reach the cable when the fault has not been isolated can result in tremendous cost if the technician has identified the wrong stretch of cable.

Thus, there is a need in the art for a method and apparatus for isolating faults in cables that are strung between support poles. There is a need in the art for a method and apparatus for viewing faults in cables that are strung between support poles. There is a need in the art for a method and apparatus for isolating and viewing faults in cables that are positioned in locations, which are difficult to access.

SUMMARY OF THE INVENTION

In one embodiment of the present invention an Inspection system is presented. The Inspection system enables and operator to troubleshoot cables strung between support poles or located in subterranean areas that are hard to reach. The Inspection system includes an inspection device that is placed on the cable and moves along the cable taking images of the cable. The images are communicated to an operator for display and troubleshooting.

The Inspection system comprises a casing including an upper section, a lower section and a hinge formed in the casing, wherein the upper section and the lower section rotate around the hinge and separate to an open position or rotate around the hinge to a closed position; a passageway formed within the casing when the upper section and the lower section are in the closed position, the passageway capable of enveloping a cable including a top-side and a bottom-side when the upper section and the lower section are in the closed position; a movement mechanism positioned in the upper section, the movement mechanism engaging the cable when the upper section and the lower section connect in the closed position; a first camera in the upper section of the casing and positioned to take images of the top-side of the cable; and a second camera in the lower section of the casing and positioned to take images of the bottom-side of the cable.

DESCRIPTION OF THE INVENTION

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

An Inspection device is presented. In one embodiment of the present invention, the Inspection device is an Aerial Inspection device. The Aerial Inspection device enables an operator to visually inspect a cable strung between two support poles while the operator is positioned on the ground or at a remote location. The Aerial Inspection device provides a visual image of the cable so that the operator may isolate and troubleshoot a fault in the cable.

Figure 1:
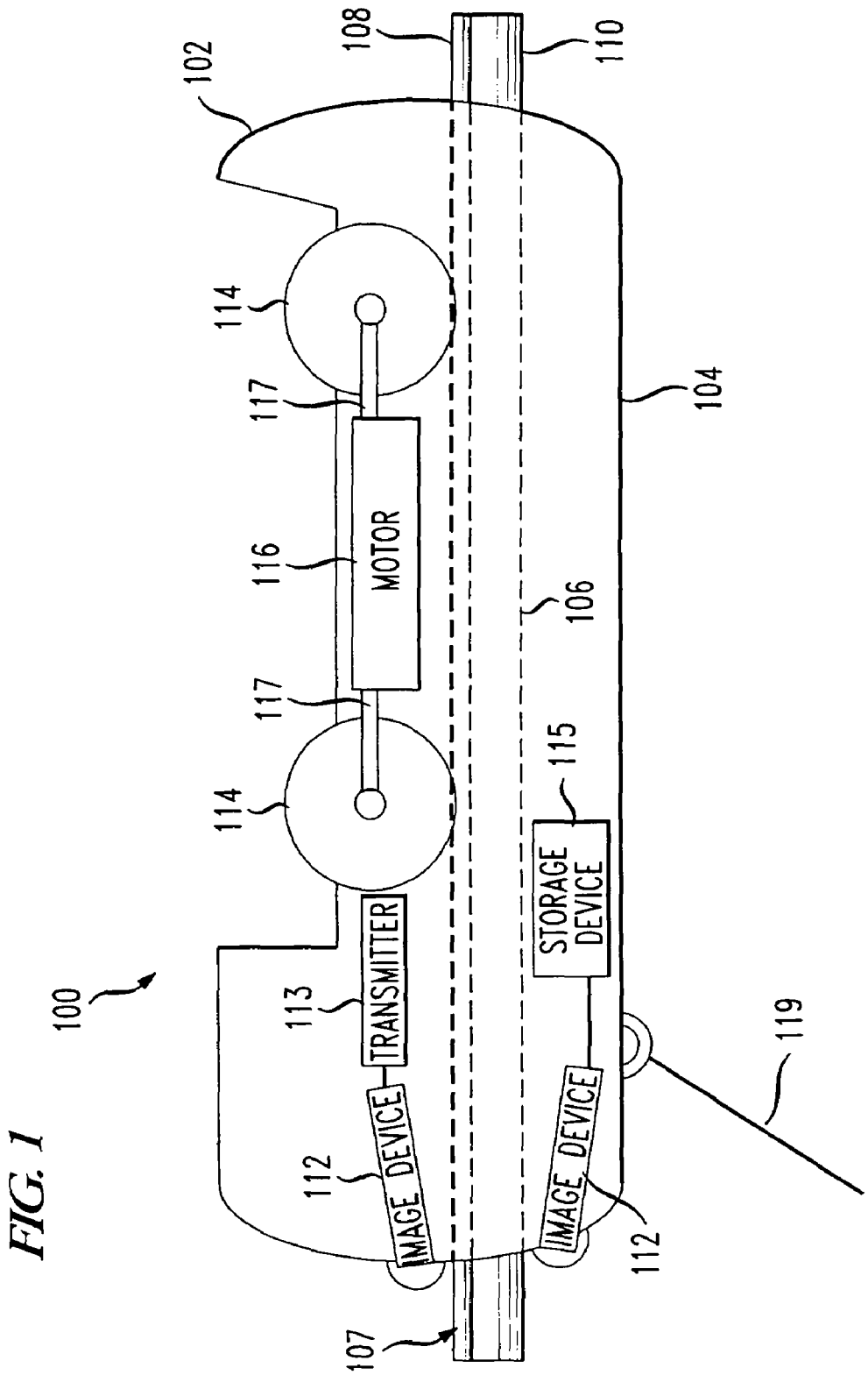
FIG. 1 is a side view of an inspection apparatus structured in accordance with the teachings of the present invention.

FIG. 1 displays a side view of an embodiment of the Aerial Inspection device 100 structured in accordance with the teachings of the present invention. The Aerial Inspection device 100 includes an upper section 102 and a lower section 104. Both the upper section 102 and the lower section 104 combine to form a casing, which includes the various components of the Aerial Inspection device 100.

In one embodiment of the present invention, the casing (e.g., including the combination of upper section 102 and lower section 104) may be made from a composite material, from a plastic material or from a metal material. In one embodiment of the present invention, the total casing may measure less than 24 inches in length and less than 12 inches in height. In addition, the Aerial Inspection device 100 may weight less than 20 pounds. It should be appreciated that while specific dimensions have been disclosed, alternative dimensions may be used and still remain within the scope of the present invention.

The upper section 102 of the casing and the lower section 104 of the casing rotate around a hinge (not shown in FIG. 1) located in the casing. The upper section 102 of the casing and the lower section 104 of the casing may rotate around the hinge to an open position in which the upper section 102 of the casing and the lower section 104 of the casing are separated. In addition, the upper section 102 of the casing and the lower section 104 of the casing may rotate around the hinge to the point where the upper section 102 of the casing and the lower section 104 of the casing make contact or connect with each other. In one embodiment of the present invention, a locking mechanism (not shown in FIG. 1) may be positioned across from the hinge to secure the upper section 102 of the casing to the lower section 104 of the casing.

When the upper section 102 of the casing is in contact (e.g., connects) with the lower section 104 of the casing, a passageway 106 forms within the casing. The passageway 106 runs the length of the casing and envelops a utility conveyance 107, which consist of a utility carrier 108 and a cable 110. The utility carrier 108 is a metal rod used to support the cable 110 when the cable 110 is strung between two support poles. The passageway 106 may be of varying diameters and shapes (e.g., square, cylindrical) and still remain within the scope of the present invention.

A movement mechanism is presented in the present invention. The movement mechanism moves the Aerial Inspection device 100 along the utility conveyance 107. In one embodiment of the present invention, the movement mechanism includes wheels 114. The wheels 114 are positioned within the upper section 102 of the casing. However, the wheels may also be positioned within the lower section 104 of the casing. In one embodiment of the present invention, the wheels 114 may be made from foam rubber, metal or a composite material. The passageway 106 is sized such that the Aerial Inspection device (e.g., with the exception of the movement mechanism and passageway 106) does not make contact with the utility conveyance 107. However, in one embodiment of the present invention, the wheels 114 protrude beyond the boundary of the casing into the passageway 106 and make contact with the utility conveyance 107.

In one embodiment of the present invention, the wheels 114 make contact with the utility conveyance 107 (e.g., utility carrier 108) when the upper section 102 of the casing is interlocked with to the lower section 104 of the casing and the two sections are connected. In addition, the wheels 114 are connected to the casing and can support the weight of the Aerial Inspection device 100. As such, the wheels 114 make contact with the utility carrier 108 and support the Aerial Inspection device 100 above the utility conveyance 107.

The wheels 114 are positioned on spindles that connect to the upper section 102 of the casing. As such, the wheels 114 are able to rotate around the spindles. In addition, since the spindles are connected to the upper section 102 of the casing, the Aerial Inspection device 100 may move along the utility conveyance 107 when the wheels 114 rotate. It should be appreciated that the wheels 114 may rotate in a clockwise or counter-clockwise direction, moving the Aerial Inspection device 100 forward or backward.

In one embodiment of the present invention, a motor 116 is connected between the wheels 114. The motor 116 is connected to a drive mechanism such as a drive shaft 117, which is connected to the wheels 114. The motor 116 generates power, which causes the drive shaft 117 to rotate. As the drive shaft 117 rotates, the wheels 114 rotate and cause the Aerial Inspection device 100 to move along the utility conveyance 107.

In one embodiment of the present invention, several image devices 112 are positioned in the casing (e.g., combination of upper section 102 and lower section 104). The image devices 112 may be cameras for taking and transmitting image information. The image information may include still pictures or moving pictures. In addition, the image devices 112 may be some other type of image technology such as thermal imaging technology.

The image devices 112 are positioned in the casing and may be positioned in the upper section 102 of the casing, the lower section 104 of the casing or in both sections of the casing. In an alternate embodiment, the image devices 112 may be positioned on the outside of the casing. The image devices 112 are positioned to take images of the utility conveyance 107 to detect faults. For example, in one embodiment of the present invention, the image devices 112 are positioned at the front of the casing and angled downward toward the utility conveyance 107 to observe any fault in the utility conveyance 107. In another embodiment of the present invention, the image devices 112 are positioned at the rear of the utility conveyance 107 and angled downward to view the utility conveyance 107. In another embodiment of the present invention, the image devices 112 are positioned perpendicular to the utility conveyance 107 and take images through openings in the passageway 106.

Image devices 112 in accordance with the teachings of the present invention may come in a vast array of shapes or sizes. For example, cameras shaped like a pen or a coin are within the teachings of the present invention. The cameras may have zoom capability and movement capability to zoom-in and zoom-out on a point of interest on the utility conveyance 107 or to move to a different angel on the point of interest on the utility conveyance 107. A variety of camera types may be made for use in the present invention. For example, a number of manufacturers make miniature camera systems with pan and tilt capability or color distinguishing capability. Further, a number of manufacturers provide cameras with tremendous zoom capability so that extremely small fractures (e.g., faults) can be detected.

The image devices 112 include an interface that connects to a cable. The cable transports images taken by the image devices 112 to a display console. For example, in one embodiment of the present invention, the cable may be a coaxial cable or fiber optic cable. The coaxial cable may connect to a display device such as a screen located in relative proximity (e.g., 50 to 60 feet) to the Aerial Inspection device 100.

In another embodiment of the present invention, the image device 112 may connect to a radio-transmitting device 113. The radio-transmitting device 113 may transmit the images to a receiver connected to a display device. For example, the radio-transmitting device 113 may communicate with a base station or an operations center.

In another embodiment of the present invention, the image device 112 may connect to a storage device 115. The storage device 115 may store images for real-time retrieval, subsequent retrieval or processing. For example, the storage device 115 may store information, which is then communicated to a base station or an operations center for future processing.

A display device receives the images generated by the image device 112. The display device may display the images in a number of different configurations. For example, a separate window may be shown in the display device to simultaneously display the images from each image device 112. In addition, the display device may display images from each image device 112 separately (e.g., sequentially).

A tether 119 is attached to the casing (e.g., lower section 104). The tether 119 may include several components that are combined collectively or independently. The tether 119 may include a cable, which may be used to pull the Aerial Inspection device 100 along the utility conveyance 107. In another embodiment, the tether 119 may include a coaxial cable for connecting the image devices 112 to a display device. The coaxial cable may communicate the images generated by the image devices 112 to a display device on the ground or to a display device held by an operator perched on a support pole. Lastly, the tether 119 may also include a cable for providing power to the motor 116 located in the Aerial Inspection device 100.

Figure 2:
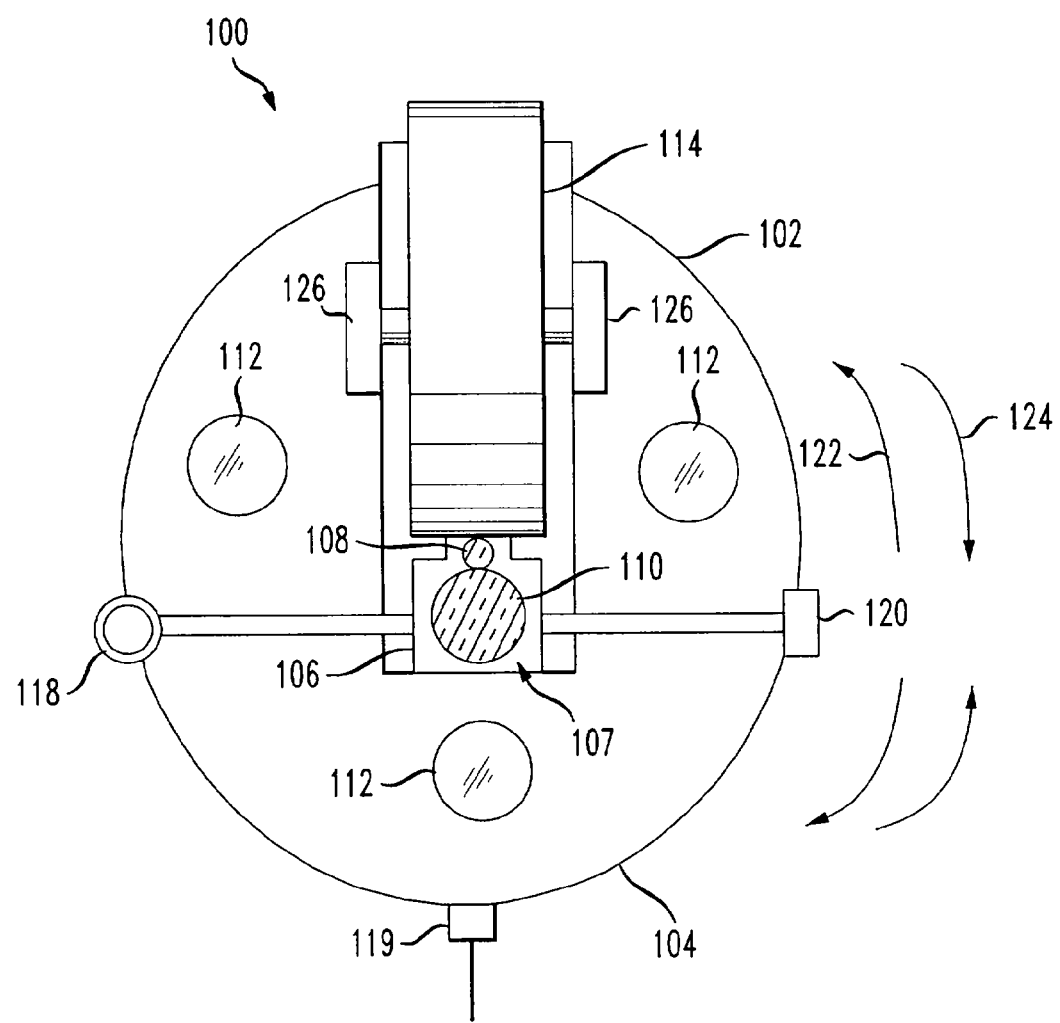
FIG. 2 is a front view of an inspection apparatus structured in accordance with the teachings of the present invention.

FIG. 2 displays a front view of the Aerial Inspection device 100 implemented in accordance with the teachings of the present invention. In FIG. 2 the upper section 102 of the casing is shown and the lower section 104 of the casing is shown.

The upper section 102 of the casing and the lower section 104 of the casing are connected by a hinge 118. The upper section 102 of the casing and the lower section 104 of the casing rotate around the hinge 118 to an open position as shown by arrows 122. In one embodiment of the present invention, the hinge 118 may run the length of the Aerial Inspection device 100 or a plurality of hinges may run along the length of the Aerial Inspection device 100. In an alternative embodiment, a single hinge 118 may be used in the Aerial Inspection device 100. The hinge 118 may be placed on any location of the casing to separate the casing into two sections.

In one embodiment of the present invention, a locking mechanism 120 is positioned across from the hinge 118. As such, when the upper section 102 of the casing and the lower section 104 of the casing are rotated around the hinge 118 as shown by directional arrows 124 to a closed position, the locking mechanism 120 may be used to fasten the upper section 102 of the casing to the lower section 104 of the casing and connect the two sections. When the casing is in the closed position and the upper section 102 of the casing is connected to the lower section 104 of the casing, the casing forms a passageway 106, which envelops utility conveyance 107. As such, the utility carrier 108 and the cable 110 are positioned in the passageway 106 formed by connecting the upper section 102 of the casing with the lower section 104 of the casing.

The wheels (e.g., movement mechanism 114) then make contact with the utility carrier 108 and ride along the utility carrier 108. The wheels 114 may be connected to a hinge mechanism 126, which enables the wheels 114 to move upward and downward to make contact with the utility carrier 108. The hinge mechanism 126 may be spring-loaded so that pressure is applied to the utility carrier 108 as the wheels 114 make contact with the utility carrier 108.

A plurality of image devices 112 are shown in the Ariel Inspection device 100. The image devices 112 are angled and focused on the cable 110 to record image information (e.g., images) of the cable 110 for viewing. In one embodiment of the present invention, three image devices 112 are implemented as shown in FIG. 2 for viewing the cable 110. In one embodiment of the present invention, the image devices 112 may be connected to a storage device 115 (not shown in FIG. 2) housed in the casing. The storage device 115 may store images for transfer to personnel on the ground or back to an operations center.

In one method of the present invention, an operator climbs a support pole. The operator positions The Aerial Inspection device 100 by unlocking the locking mechanism 120. The upper section 102 and the lower section 104 of the casing are then separated by rotating the upper section 102 of the casing and the lower section 104 of the casing around the hinge 118 consistent with directional arrows 122. The Aerial Inspection device 100 is then positioned so that the passageway 106 of the Aerial Inspection device 100 aligns with the utility conveyance 107 (e.g., utility carrier 108 and cable 110). Once the passageway 106 of the Aerial Inspection device 100 aligns with the utility conveyance 107, the upper section 102 of the casing and the lower section 104 of the casing are rotated to a close position by rotating the upper section 102 and the lower section 104 around the hinge 118 in a direction consistent with directional arrows 124. The upper section 102 of the casing and the lower section 104 of the casing are then connected and locked together using locking mechanism 120. As such, the wheels 114 will rest on the utility carrier 108 and the image devices 112 will be positioned to take pictures of the cable 110.

Once the Aerial Inspection device 100 is positioned around the utility conveyance 107 and riding on the utility carrier 108, images may be taken of the cable 110. The images may be transported down to an operator on the ground through the tether 119 or radio transmitted to an operator on the ground using a radio-transmitting device 113 (not shown in FIG. 2). In an alternate embodiment, the images may be communicated to a remote location using the radio-transmitting device 113. Lastly, the images may be stored in a storage device 115 (not shown in FIG. 2) for future processing. As the images are taken, the Aerial Inspection device 100 may be moved along the utility conveyance 107. For example, power may be supplied through the tether 119 to the motor (e.g., 116 of FIG. 1) at which point the motor (e.g., 116 of FIG. 1) rotates the drive shaft 117 (not shown in FIG. 2), which moves the Aerial Inspection device 100 along the utility conveyance 107. In alternative method, the tether 119 may be used to pull the Aerial Inspection device 100 along the utility conveyance 107. Lastly, the motor (e.g., 116 of FIG. 1) may be radio controlled and a radio signal may be used to move the Aerial Inspection device 100 along the utility conveyance 107.

As the Aerial Inspection device 100 is moved along the utility conveyance 107, images are taken of the utility conveyance 107. The images may be still images or moving images. The images may be displayed in a variety of methods. For example, the images may be displayed simultaneously in real-time, displayed sequentially in real-time or stored and reviewed later. In one method of the present invention, the images may be reviewed with the human eye. In an alternative method of the present invention, the images may be input into software for image processing.

Once a fault in the utility conveyance 107 is located, the Aerial Inspection device 100 may be stopped or moved in reverse to identify the fault. In addition, the image devices 112 may be moved or focused to more clearly identify the fault in the utility conveyance 107. The location of the fault may then be analyzed in real-time or recorded. The Aerial Inspection device 100 may then be moved back to a support pole, where the Aerial Inspection device 100 can be removed by an operator. Further, the images may be analyzed for more advanced troubleshooting.

Thus, the present invention has been described herein with reference to a particular embodiment for a particular application. Those having ordinary skill in the art and access to the present teachings will recognize additional modifications, applications and embodiments within the scope thereof.

It is, therefore, intended by the appended claims to cover any and all such applications, modifications and embodiments within the scope of the present invention.

What is claimed is:

1. An inspection system comprising:
   a casing including an upper section, a lower section and a hinge, wherein the upper section and the lower section rotate around the hinge to a closed position;
   a passageway formed within the casing when the upper section and the lower section are in the closed position, the passageway capable of enveloping a cable;
   a movement mechanism positioned in the upper section, the movement mechanism capable of engaging the cable when the upper section and the lower section are in the closed position; and
   a camera in the upper section of the casing, the camera positioned to take images of the cable.

2. An inspection system as set forth in claim 1, wherein the movement mechanism comprises two wheels for moving the inspection system along the cable.

3. An inspection system as set forth in claim 1, the movement mechanism further comprising;
   a motor generating power;
   a drive shaft coupled to the motor and rotating in response to the power generated by the motor; and
   two wheels coupled to the drive shaft and rotating in response to rotating the drive shaft.

4. An inspection system as set forth in claim 1, wherein the camera is positioned at an angle relative to the passageway.

5. An inspection system as set forth in claim 1, further comprising a second camera in the lower section of the casing, the second camera positioned to take images of the cable.

6. An inspection system as set forth in claim 1, wherein the image is positioned to take images of the cable through the passageway.

7. An inspection system as set forth in claim 1, the movement mechanism further comprising two wheels positioned in the uppers section of the casing, the two wheels rotating and moving the inspection system along the cable; and a loading mechanism coupling the two wheels to the upper section of the casing, the loading mechanism enabling the two wheels to contact the cable and apply pressure against the cable.

8. An inspection system as set forth in claim 1, wherein the camera generates images and communicates the images for viewing in a display.

9. An inspection system as set forth in claim 1, wherein a tether is connected to the casing, the tether enabling an operator to move the inspection system along the cable.

10. An inspection system as set forth in claim 1, wherein a tether is connected to the casing, the tether including a cable for communicating images from the camera.

11. An inspection system as set forth in claim 1, wherein a tether is connected to the casing, the tether including a cable for communicating power to the casing.

12. An inspection system as set forth in claim 1, wherein a tether is connected to the casing, the tether including a cable for providing a pull line to pull the casing along the cable.

13. An inspection system as set forth in claim 1, the inspection system further comprising a transmitter coupled to the camera, the transmitter generating a transmission in response to images of the cable generated by the camera.

14. An inspection system as set forth in claim 1, the inspection system comprising a storage device coupled to the camera and storing image information.

15. A method of performing cable inspection comprising the steps of:
    receiving images generated by an inspection system, the inspection system comprising a passageway capable of enveloping a cable; a movement mechanism capable of moving the inspection system along the cable; and an image device positioned to take images of the cable as the movement mechanism moves the inspection system along the cable; and
    analyzing the cable in response to receiving the images generated by the inspection system.

16. A method of performing cable inspection as set forth in claim 15, wherein the step of analyzing the cable includes analyzing the cable for a fault.

* * * * *